United States Patent [19]

Ikuno et al.

[11] Patent Number: 4,870,488
[45] Date of Patent: Sep. 26, 1989

[54] ENDOSCOPE IMAGING SYSTEM USED WITH AN ELECTRONIC SCOPE AND AN OPTICAL ENDOSCOPE

[75] Inventors: Yuji Ikuno, Oume; Hiroki Hibino, Hachioji, both of Japan

[73] Assignee: Olympus Optical Co., Ltd., Tokyo, Japan

[21] Appl. No.: 153,893

[22] Filed: Feb. 9, 1988

[30] Foreign Application Priority Data

Feb. 10, 1987 [JP] Japan ................... 62-029373

[51] Int. Cl.⁴ .............................................. H04N 7/18
[52] U.S. Cl. .......................................... 358/98; 128/6
[58] Field of Search ...................... 358/98, 160, 21 R; 128/4, 6

[56] References Cited

U.S. PATENT DOCUMENTS 4,727,418  2/1988  Kato et al. .......................... 358/98
4,746,975  5/1988  Ogiu ................................... 358/98

FOREIGN PATENT DOCUMENTS 60-243625  12/1985  Japan .

Primary Examiner—James J. Groody
Assistant Examiner—Victor R. Kostak
Attorney, Agent, or Firm—Armstrong, Nikaido, Marmelstein, Kubovcik & Murray

[57] ABSTRACT

A system provided with an electronic scope containing a solid state imaging device on the tip side of the insertable part and a television camera containing an solid state imaging device and fitted to the eyepiece part of an optical endoscope provided with an optical image transmitting device within the insertable part. The number of pixels of the solid state imaging device of the television camera is made larger than the solid state imaging device of the electronic scope.

25 Claims, 12 Drawing Sheets

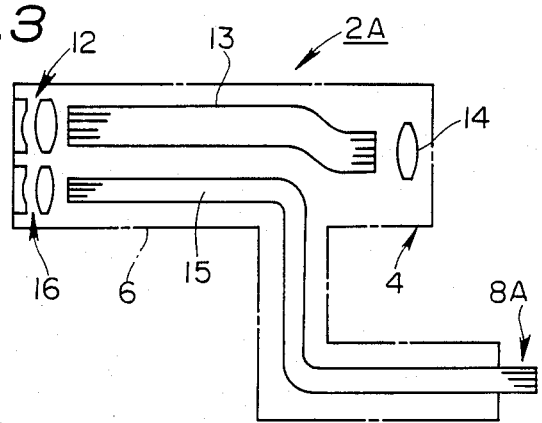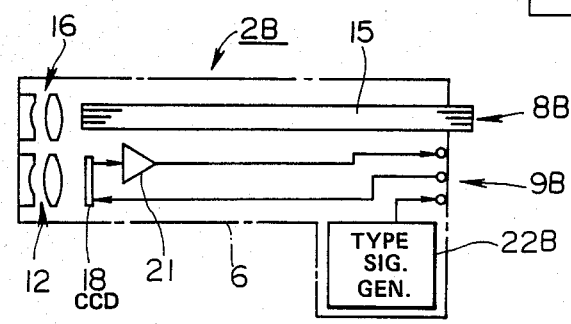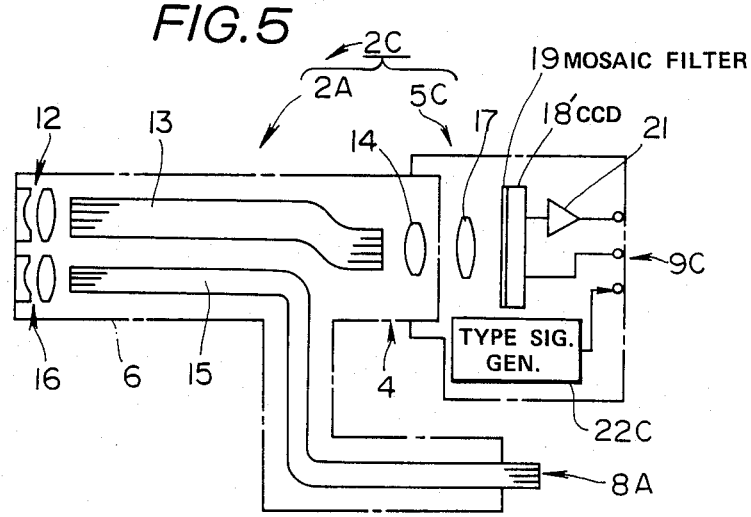

FIG.10
(a) 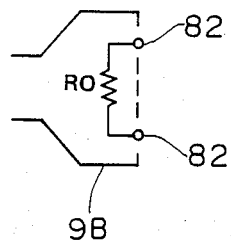
(b) 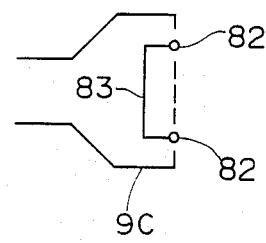
FIG.11
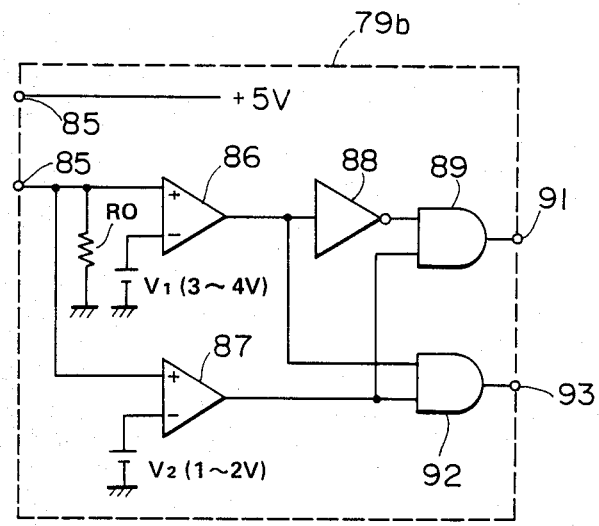
FIG.12
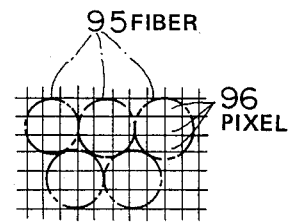

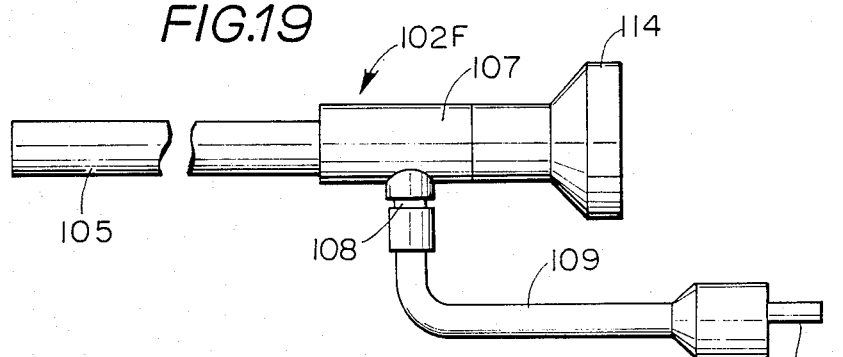
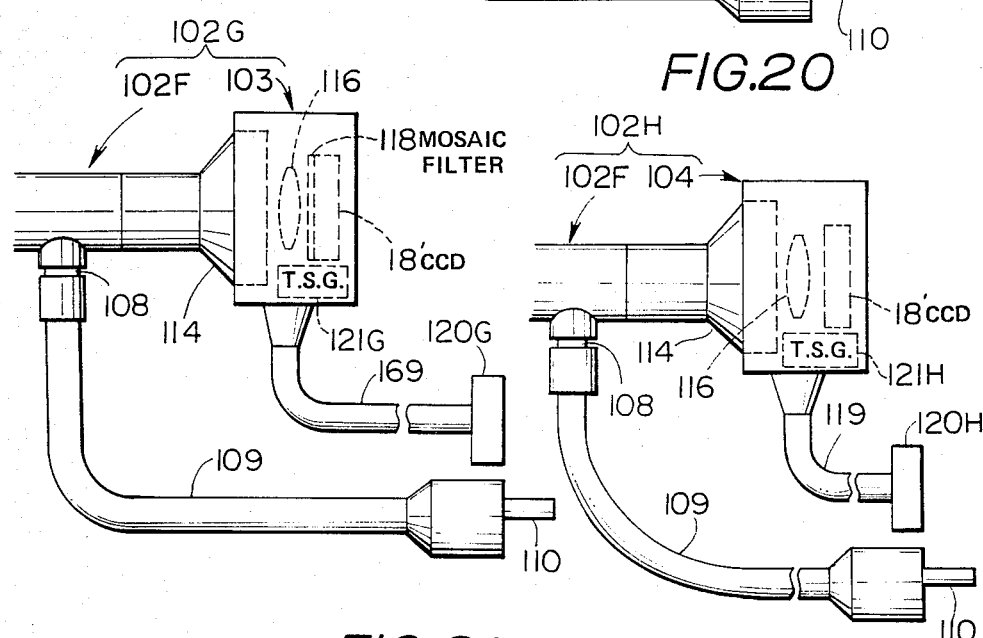
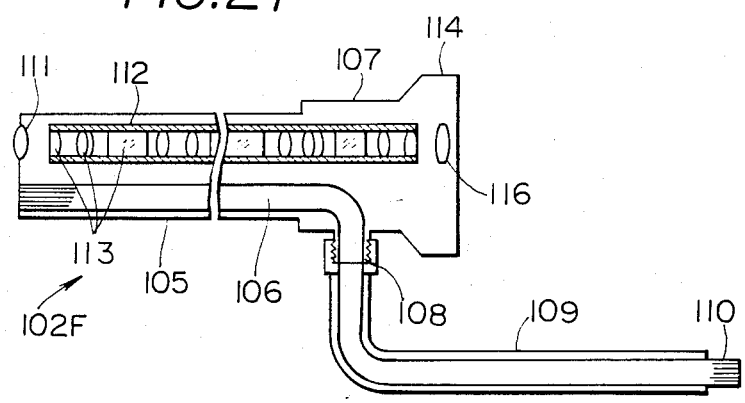

ENDOSCOPE IMAGING SYSTEM USED WITH AN ELECTRONIC SCOPE AND AN OPTICAL ENDOSCOPE

FIELD OF THE INVENTION AND RELATED ART STATEMENT

This invention relates to an endoscope imaging system which can be used by either of an electronic scope provided with an imaging means and an optical endoscope externally fitted with a camera provided with an imaging means.

BACKGROUND OF THE INVENTION

Recently, instead of an optical endoscope (called also a fiber scope) wherein an optical image formed by an objective in the tip part of an insertable part is transmitted to the base end side through an image guide formed of a fiber bundle, there has been developed an electronic endoscope (which shall be called an electronic scope hereinafter) wherein an optical image formed by an objective is photoelectrically converted to an electric signal by a solid state imaging device (which shall be abbreviated as an SID hereinafter) such as a charge coupled device (which shall be abbreviated as a CCD hereinafter) and the electric signal is transmitted to the base and can be displayed through a video processor.

With the above mentioned electronic scope, not only is a light source apparatus required, as in the fiber scope, but also a signal processing means for processing signals is required.

Now, even in the above mentioned fiber scope, if a TV camera is fitted to the eyepiece part of this fiber scope, signals can be processed by the signal processing means common with the electronic endoscope. Such an apparatus is disclosed in the gazette of a Japanese patent laid open No. 243625/1985.

In the above mentioned prior art example, by using a common signal processing means, there can be made an economical apparatus wherein either of an electronic scope or a fiber scope externally fitted with a TV camera can be used.

In the above mentioned prior art example, an economical apparatus can be realized but there have been defects. Since as a common signal processing means is used, the number of pixels of the SID used in the externally fitted camera will be the same as the number of pixels of the SID and, even when a fiber scope is filled thereto even though the number of fibers forming the image guide of the fiber scope is large. Thus, the resolution cannot be improved externally fitted camera is attached.

OBJECT AND SUMMARY OF THE INVENTION

An object of the present invention is to provide an endoscope imaging system wherein a video image is obtained which does not reduce the resolution of the image guide of a fiber scope.

Another object of the present invention is to provide an endoscope imaging system which can be used in common with an electronic scope.

In the present invention, the number of the pixels of solid state imaging device, in an externally fitted television camera which is attachable to the eyepiece part of an optical endoscope is made larger than the number of pixels of a solid state imaging device used for the imaging device of an electronic scope. Thus that an imaged picture image having high resolution can be obtained without sacrificing the resolution of the image guide by the optical endoscope.

BRIEF DESCRIPTION OF THE DRAWINGS

FIGS. 1 to 12 relate to the first embodiment of the present invention.

FIG. 1 is a perspective view showing the entire system of the first embodiment.

FIG. 2 is a formation view of an imaging apparatus body.

FIG. 3 is a schematic formation view of a fiber scope.

FIG. 4 is a schematic formation view of a frame sequential type electronic scope.

FIG. 5 is a schematic formation view of a fiber scope fitted with a mosaic type TV camera.

FIG. 6 is a formation view showing a light source apparatus part.

FIG. 7 is a perspective view showing the schematic formation of a movable filter part.

FIG. 8 is a formation diagram of a frame sequential type process circuit.

FIG. 9 is a formation diagram of a mosaic type process circuit.

FIG. 10 is an explanatory view showing an example of a type signal generating means.

FIG. 11 is a circuit diagram showing an example of a discriminating circuit.

FIG. 12 is an explanatory view showing the manner in which the image of the end surface of an image guide of a fiber scope is formed on the imaging surface of a TV camera.

FIG. 19 is a side view showing a rigid endoscope usable in the first embodiment and a rigid endoscope fitted with a mosaic type TV camera.

FIG. 20 is a side view showing a rigid endoscope fitted with a frame sequential type TV camera usable in the third embodiment.

FIG. 21 is a formation view showing the rigidity of the rigid endoscope shown in FIG. 19.

DETAILED DESCRIPTION OF PREFERRED EMBODIMENTS

Figure 1:
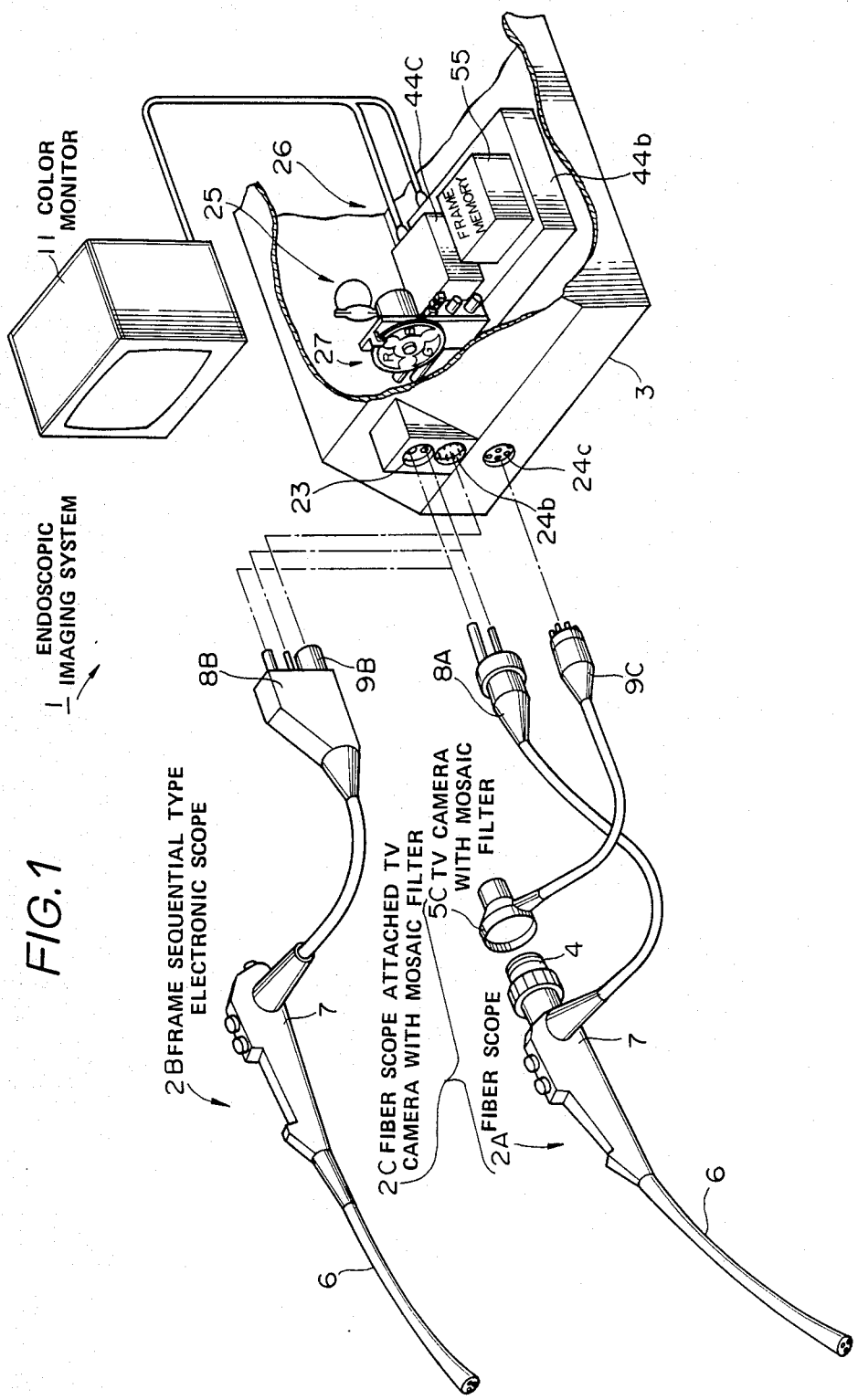

As shown in FIG. 1, an endoscopic imaging system 1 of the first embodiment comprises various scopes 2A, 2B and 2C, an imaging apparatus body 3 to which these scopes 2A, 2B and 2C can be connected and a color monitor 11 color-displaying video signals processed in the imaging apparatus body 3.

The above mentioned scope 2A is a fiber scope, the scope 2B is a frame sequential type electronic scope and the scope 2C is a fiber scope (which shall be mentioned hereinafter as a fiber scope fitted with a mosaic type TV camera i.e. a fiberscope (fitted with a TV camera having a color filter or a fiber scope attached with a TV camera with a mosaic filter) fitted with a TV camera (which shall be mentioned as a mosaic type TV camera or a TV camera with a color mosaic filter hereinafter) 5C in the eyepiece part 4 of the above mentioned fiber scope 2A. In FIG. 1, the fiber scope 2C fitted with a mosaic type TV camera shows the fiber scope 2A and TV camera 5C part as separated from each other.

In each of the above mentioned scopes 2A, 2B and 2C (represented by the reference numeral 2 hereinafter in case they are in common), a flexible elongate insertable part 6 and an operating part 7 on the rear end side of the insertable part 6 are formed. A universal cord (a light guide cable in the fiber scope 2A) is extended out of this operating part 7 and is provided at the tip with light source connector 8A or 8B. In the above mentioned frame sequential type electronic scope 2B and fiber scope 2C fitted with a mosaic type TV camera, signal connectors 9B and 9C are respectively provided on the tip sides of the universal cords.

In the case of the above mentioned fiber scope 2A, a naked eye observation can be made from the eyepiece part 4 but, in the other scopes 2B and 2C, by fitting the imaging apparatus body 3 with a color monitor 11, the imaged object image can be color-displayed.

The above mentioned respective scopes 2A, 2B and 2C are respectively of the formations shown in FIGS. 3, 4 and 5.

In the above mentioned fiber scope 2A, as shown in FIG. 3, an objective 12 as an image forming light source system is arranged in the tip part of the insertable part 6 as shown in FIG. 3. The tip surface of the image guide 13 is present in the focal plane of this objective 12. The object image formed on the tip surface of this image guide 13 is transmitted to the rear end surface of this image guide 13. The optical image transmitted through the eyepiece 14 arranged opposite the rear end surface of this image guide 13 can be observed with a naked eye.

A light guide 15 as an illuminating light transmitting means is inserted through the above mentioned insertable part 6. An illuminating light from the light source apparatus is fed to the rear end surface of this light guide 15. This illuminating light is radiated on the object side through a light distributing lens 16 from the tip surface of the light guide 15.

As shown in FIG. 5, by the mosaic type TV camera 5C fitted to the eyepiece part 4 of the above mentioned fiber scope 2A, an optical image transmitted by the image guide 13 through a magnifying image forming lens 17 is formed on the imaging surface of a CCD 18′ having a large number of pixels. A color mosaic filter 19 is pasted on the imaging surface of this CD 18′ and the image is decomposed into pixels of R, G and B. The signal photoelectrically converted by the CCD 18′ is read out by applying driving pulses to the above mentioned CCD 18′, is amplified through a pre-amplifier 21 and is then transmitted to the signal connector 9C side through the signal cable.

Also, as shown in FIG. 4, in the electronic scope 2B, a CCD 18 is arranged in the focal plane of the objective 12 and the signal photoelectrically converted by this CCD 18 is amplified by this CCD 18. This CCD 18 is of dimensions such as can be contained in the tip part of the insertable part 6. Therefore, from the necessity of reducing the pain to a patient during insertion or the like, the number of pixels can not be made too large.

On the other hand, since the above mentioned TV camera 5C is not to be inserted into the body cavity, a housing space larger than the housing space of the insertable part 6 can be provided and the CCD 18′ of a larger number of pixels than the number of pixels of the above mentioned CCD 18 is housed.

The illuminating means in the above mentioned electronic scope 2B is the same as in the case of the fiber scope 2A and is indicated by the same reference numeral.

The above mentioned electronic scope 2B and externally fitted camera 5C are provided with type signal generating circuits 22B and 22C outputting type signals different from each other so that, in case a signal connector is connected, a type signal will be output to the body 3 side and, by this type signal, the illumination and signal process corresponding to the scope can be made.

A light source connector receptacle 23, frame sequential type signal connector receptacle 24b and mosaic type signal connector receptacle 24C are provided, for example, on the front surface of the imaging apparatus body 3 so that the above mentioned respective scopes 2 may be connected.

A light source apparatus part 25 and signal processing apparatus part 26 are contained within the above mentioned imaging apparatus body 3.

Figure 6:
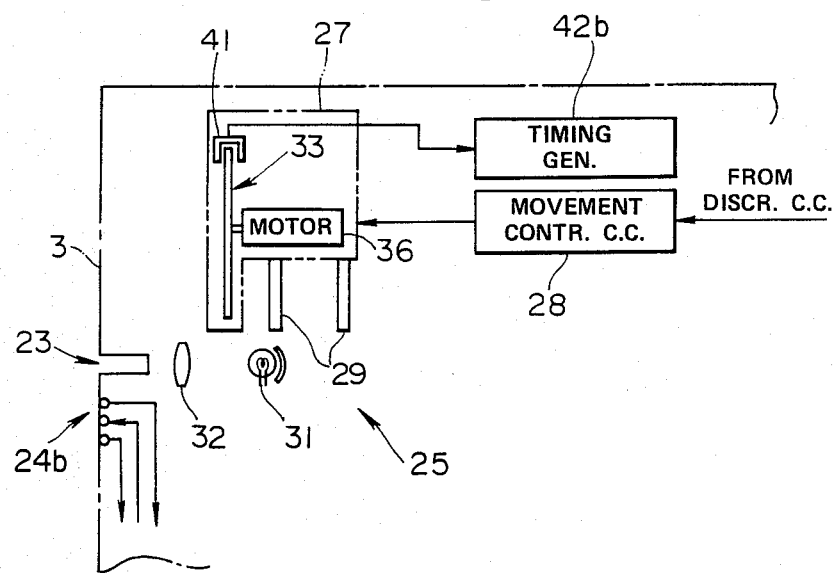

The above mentioned light source part 25 is provided with a movable filter part 27 and is made movable on rails 29 by a movement controlling circuit 28 as shown in FIG. 6.

Figure 2:
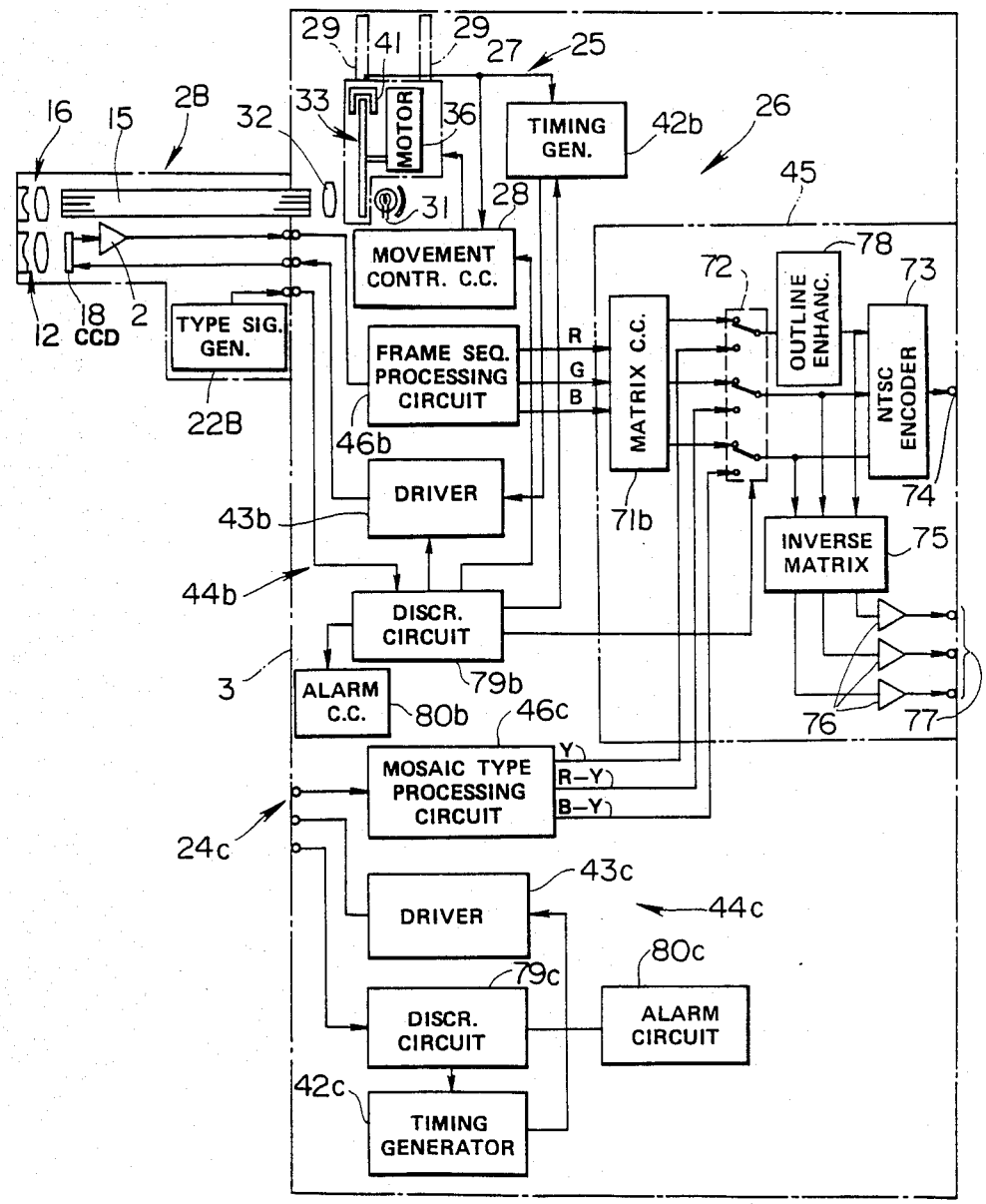
Figure 7:
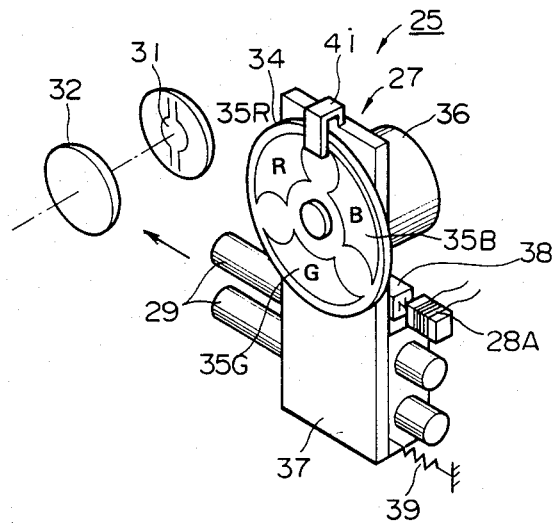

As shown in FIG. 6 or 7, in the light source apparatus part 25, normally, the white light of the light source lamp 31 is condensed and radiated to the light source connector (that is, the light guide connector) connected to the connector receptacle 23 through the condenser lens 32. In this state, the movable filter part 27 has retreated from the light path. On the other hand, when moved by the movement controlling circuit 28, as shown in FIG. 2, the movable filter part 27 will be interposed in the light path. In this state, the white light of the light source lamp 31 will be radiated onto a rotary filter 33 forming the movable filter part 27. In this rotary filter 33, as shown in FIG. 7, on a disc frame 34, three fan-shaped windows are formed and R, G and B color transmitting filters 35R, 35G and 35B are fitted to these windows. By rotating and driving this disc frame 34 with a motor 36, an object will be illuminated frame sequentially by R, G and B illuminating lights.

The above mentioned movable filter part 27 is fitted to a movable stand 37 and is made movable in the horizontal direction in FIG. 7 on the rails 29.

For example, a magnet 38 is fitted to this movable stand 37. On the other hand, for example, the N pole of this magnet 38 is opposed to an electromagnetic coil 28A forming the movement controlling circuit 28. When a driving current is made to flow through this electromagnetic coil 28A, the movable filter part 27 which is normally retreated from the light path by a spring 39 will be all to be interposed into the light path.

A position sensor 41 in which a light emitting device and light receiving device are arranged so as to hold the disc frame 34 in one place on the peripheral edge of the disc frame 34 rotated and driven by the above mentioned motor 36 is movably fitted to the movable stand 37. This position sensor 41 detects the positions of a plurality of holes (not illustrated) formed in the disc frame 34 and outputs a signal at the point in time of the termination of the illuminations of R, G and B. This signal is input into a timing generator 42b which outputs a control signal synchronized with the signal of the position sensor 41 on the basis of this signal. For example, in the CCD driver (which shall be mentioned merely as a driver hereinafter) 43b, at the point in time when the illuminations of R, G and B respectively end, driving pulses are applied to the CCD 18 from the driver 43b to read out the signal.

Now, the signal processing apparatus part 26 in the first embodiment consists of a frame sequential type signal processing part 44b and mosaic type signal processing part 44c.

As shown in FIG. 2, the above mentioned frame sequential type signal processing part 44b is a signal processing system operating the frame sequential type electronic scope 2B is connected. On the other hand, the mosaic type signal processing part 44c is a signal processing system functioning the scope 2C, fitted with the mosaic type TV camera is connected to the fiber scope 2A. The respective signal processing systems process signals corresponding to the numbers of pixels of the respective CCD 18 and 18'. In his first embodiment, a post-processing circuit 45 is commonly used in both signal processing parts 44b and 44c. This commonly used part is to process analogue signals. Signals can be commonly processed without depending on the numbers of pixels of the CCD 18 and 18'. By both signal processing parts 44b and 44c, the control signals of the timing generators 42b and 42c are applied to the drivers 43b and 43c and the timing of reading out the signals of CCD 18 and 18' is controlled. The signal read out of the CCD 18 of the frame sequential type electronic scope 2B is input into a frame sequential type processing circuit 46b and is processed to be a video signal by this processing circuit 46b and color signals of R, G and B are output.

One the other hand, in the case of the fiber scope 2C fitted with the mosaic type TV camera, the signal of the CCD 18' is input into a mosaic type processing circuit 46c, signals are processed by this processing circuit 46c and a luminance signal Y and color difference signals R-Y and B-Y are output.

Figure 8:
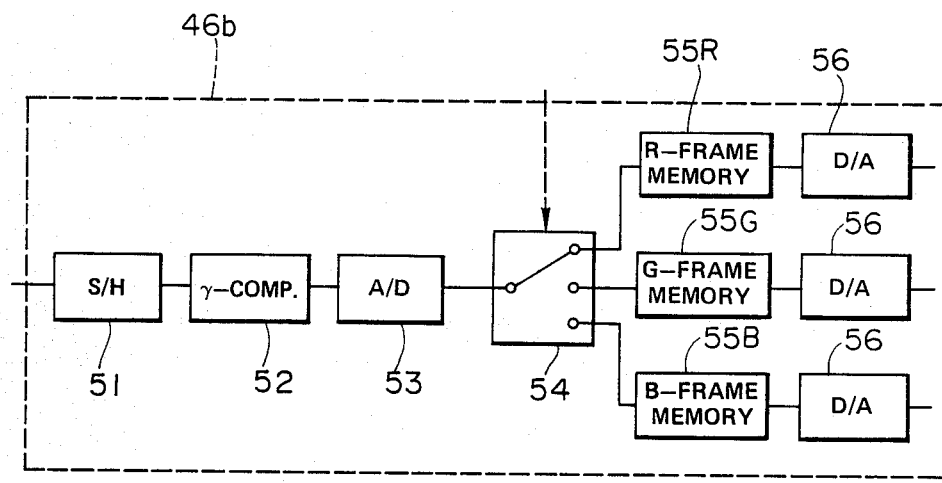

An example of the formation of the above mentioned frame sequential type process circuit 46b is shown in FIG. 8.

The signal amplified by the pre-amplifier 21 is sample-held by the sample holding circuit 51, is then γ-corrected by a γ-correcting circuit 52, is input into an A/D converter 53, is converted to a digital amount by this A/D converter 53 and is then written sequentially by 1 frame into an R-frame memory 55R, G-frame memory 55G and B-frame memory 55B through a multiplexer 54. The signal data written into the respective frame memories 55R, 55G and 55B are simultaneously read out and are respectively converted to analogue signals by a D/A converter 56 and these R, G and B signals are input into the post-processing circuit 45 which outputs two different video signals. The above mentioned R, G and B frame memories 55R, 55G and 55B correspond to the frame memory represented by the reference numeral 55 in FIG. 1.

Figure 9:
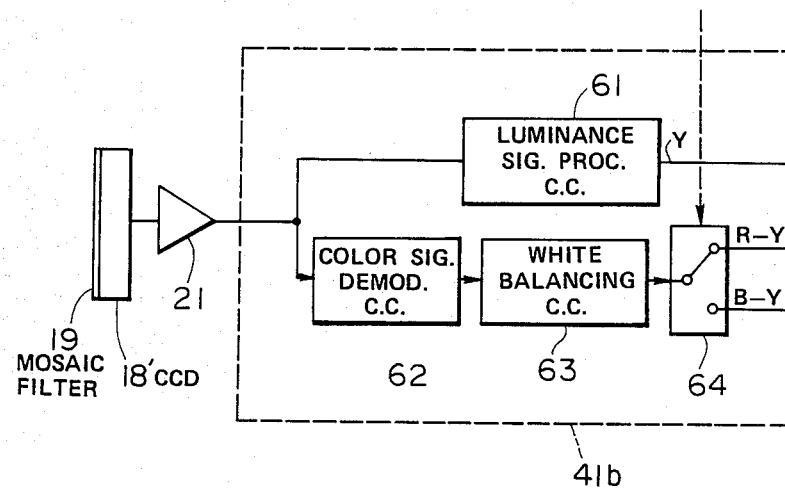

On the other hand, the mosaic type processing circuit 46c is of a formation shown, for example, in FIG. 9.

The signal amplified through the pre-amplifier 21 is transmitted through a luminance signal processing circuit 61 to produce a luminance signal Y and is input also into a color signal reproducing circuit 62 to produce color difference signals R-Y and B-Y in time series in each horizontal line and is white balance-compensated in a white balance circuit 63. One part of the signal directly and the other part as delayed by one horizontal line by a 1H delay line, not illustrated, are input into an analogue switch, not illustrated, and color difference signals R-Y and B-Y are obtained by a switching signal of the timing generator 42c.

The output signal of the above mentioned frame sequential type processing circuit 46b is input into a matrix circuit forming the post-processing circuit 45, is converted to a luminance signal Y and color difference signals R-Y and B-Y and is input into one contact side of a 3-circuit 2-contact switching switch 72. The signal of the mosaic type processing circuit 46c is input into the other contact side of this switching switch 72. This switching switch 72 is normally conductive on the mosaic type processing circuit 46c side but is switched to be conductive on the frame sequential side as shown in FIG. 2 by discriminating the type signal when the frame sequential type electronic scope 2B is connected. The signal having passed through this switching switch 72 is input into an NTSC encoder 73 and is converted to a composite video signal of the NTSC type which is output from the NTSC output end 74. The above mentioned NTSC encoder 73 is provided with a driver such as a buffer. The signal on the side made conductive by the above mentioned switching switch 72 is input into an inverse matrix circuit 75, is converted to R, G and B three primary color signals which are output from RGB output ends 77 respectively through buffers 76 forming drivers.

Now, an outline enhancing circuit 78 processing signals to enhance outlines for the luminance signal Y conducted by the switching switch 73 is interposed in the above mentioned post-processing circuit 45.

The above mentioned switching switch 72 is controlled in switching by a discriminating circuit 79b discriminating the scope to be connected on the basis of the type signal.

The above mentioned discriminating circuit 79b outputs an operation instructing signal to the timing generator 42b so as to make an illuminating and signal processing corresponding to the frame sequential type scope 2B when identified by the type signal, a movement instructing signal moving the movable filter part 27 to the movement controlling circuit 28, an instructing signal to operate the driver 43b or an instructing signal to rotate the motor 36. Also, this discriminating circuit 79b will warn by an alarm circuit 80b the mis-connection in case the connector 9C of the mosaic type TV camera 5C is connected to the frame sequential type connector receptacle 24b. On the other hand, for example, in case the connector 9B of the frame sequential type electronic scope 2B is connected to the mosaic type signal connector receptacle 24C, the mis-connection can be warned by the alarm circuit 80c. In FIG. 1, the signal connectors 9B and 9C of the electronic scope 2B and TV camera 2C are made different but may be of the same shape. In this case, the discriminating means is formed as follows.

In the above mentioned type signal generating circuits 22B and 22C, as shown, for example, in FIG. 10, the two terminals 82 in the signal connector 9B or 9C are connected through a resistance R0 of a proper value (for example, 220 Ω) or are short-circuited through a lead wire 83. On the other hand, the discriminating circuit 79b is of the formation shown, for example, in FIG. 11.

The input ends 85 connected with the above mentioned two terminals 82 one input end 85 is connected to a current source end of +5 V and the other input end 85 connected to non-inverting input ends of comparators 86 and 87 grounded through a resistance R0, for example, of 220 Ω.

On the other hand, a voltage V1, for example, of 3 to 4 VC is applied by a reference voltage source to the inverting input end of one comparator 86. A voltage $V_2$, for example, of 1 to 2 V is applied by a reference voltage source to the inverting input end of the other comparator 87. The output of one comparator 86 outputs a frame sequential type scope discriminating signal from the first output end 91 through an AND circuit 89 of two inputs together with the output of the other comparator 87 through an inverter 88. The outputs of the above mentioned both comparators 86 and 87 are led to the second output end 93 through an AND circuit 92 of two inputs.

In case the frame sequential type scope 2B is connected, the above mentioned first output end 91 will output a signal of "H" so as to make a frame sequential illumination and signal processing.

On the other hand, when the signal connector 9C of the mosaic type TV camera 9C of the mosaic type TV camera 5C is connected by mistake to the frame sequential type connector receptacle 24b, the second output end 93 will output a warning instructing signal to be "H".

When the two output 91 and 92 in the discriminating circuit 79 shown in FIG. 11 are exchanged, the circuit can be used as a discriminating circuit 79 on the mosaic type signal processing part 44c side.

In the above mentioned discriminating circuit 79b, when a frame sequential type is connected to the input ends 85, the respective comparators 86 and 87 will become respectively "L" and "H" (when not connected, both will be "L") and the output of the first output end 91 will become "H". In case the connector of one mosaic type TV camera 5C is connected, the outputs of both comparators 86 and 87 will be both "H" and the output of the second output end 92 will also become "H".

In the thus formed first embodiment, only a small dimensioned CCD 18 can be contained in the elongate insertable part 6 as shown in FIG. 4 but, in the externally fitted camera 5C, the size is not so restricted since the outside diameter having a larger insertable part 6 and a CCD 18' of the number of pixels larger than that in the CCD 18 is used.

For example, as the manner in which the optical image transmitted by the image guide 13 of the fiber scope 2A is formed on the imaging surface of the externally fitted camera 5C is as shown in FIG. 12, many pixels 96 of the square CCD 18' are contained within the circle of each fiber 95. Therefore, the optical information transmitted by each fiber 95 can be positively received by the CCD 18'.

Therefore, even in case the fiber scope 2A is used as observed with a naked eye or the externally fitted camera 5C is fitted to this fiber scope 2A and the signal is color-displayed by the color monitor 11, the resolution will not be reduced and the resolution can be returned when a naked eye observation is made with the fiber scope 2A can be retained.

In the above mentioned first embodiment, if the scope is correctly connected, it can be used, in such a case, if the connection of the signal connector is mistaken, a warning will result and therefore the use with the misconnection can be prevented. Further, in this first embodiment, the video signal outputs are unified into an NTSC type composite video output or RGB output and therefore an ordinary color monitor can be used. As the signal output ends are made common, the connection of the color monitor need not be changed in response to the scope to be connected and used.

In the above mentioned first embodiment, the luminance signal is processed to enhance the outline but, after the switching switch 72, the signals Y, R-Y and B-Y may be processed. The case of processing signals to enhance the outline and the case of not processing them can be selected. In the case of not processing signals, the number of times of converting signals may be reduced as much as possible to reduce the signal deterioration.

In the above mentioned first embodiment, the signal converting output side is commonly used but may be made separate.

Figure 13:
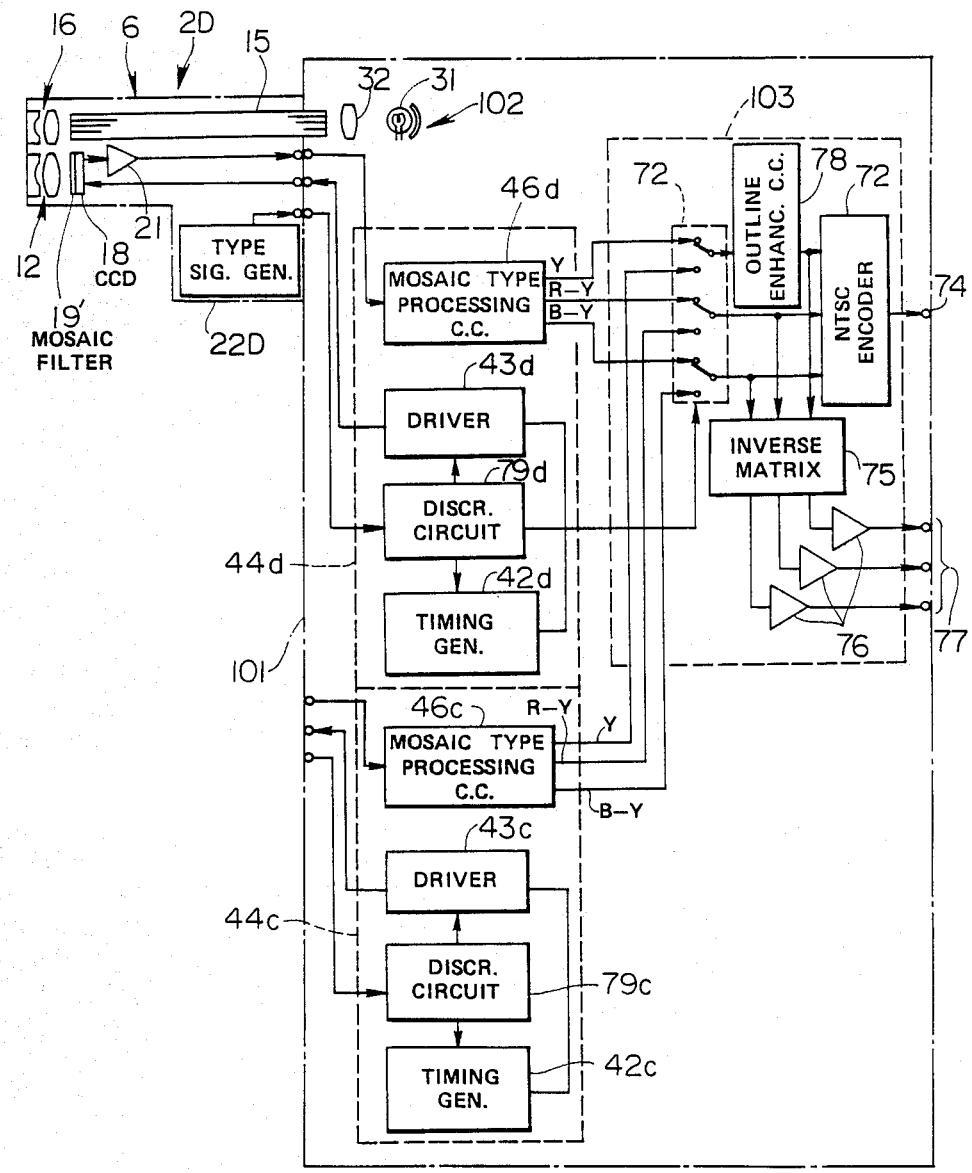
FIG. 13 is a formation view of an imaging apparatus body in the second embodiment of the present invention.

FIG. 13 shows the second embodiment of the present invention.

In this second embodiment, the mosaic type electronic scope and the fiber scope fitted with the mosaic type TV camera can be used.

The above mentioned mosaic type electronic scope 2D is the frame sequential type electronic scope 2B shown in FIG. 4 as provided with a color mosaic type filter 19' on the imaging surface of the CCD 18 and is shown in FIG. 13.

In this embodiment, for the illumination with a white light, the imaging apparatus body 101 has a white illuminating light source part 102 and two mosaic type signal processing parts 44c and 44d processing signals in response to the number of pixels.

The above mentioned light source part 102 is the same as in the white illuminating state when the movable filter part 27 is retreated from the light path.

The two signal processing parts 44c and 44d are fundamentally of the same formation provided in response to different numbers of pixels. For example, the same as in the case of the above mentioned first embodiment, one signal processing part 44c is for the TV camera 5c and the frequency and pulse number of the driving pulses of the driver 43c corresponding to many pixels are higher than in the case of the driver 43d of the other signal processing part 44d.

The mosaic type processing circuits 46c and 46d are formed of filters or the like of the band characteristics corresponding to the number of pixels in the same manner as the color signal reproducing circuit forming respective circuits separates the signals read out by the driving pulses of the above mentioned driver 43c and also the timing of separating into color difference signals is switched as synchronized with the driving pulses of the above mentioned respective drivers 43c and 43d.

The commonly used post-processing circuit 103 is formation of the post-processing circuit 45 shown in the above mentioned FIG. 2 wherein the matrix circuit 71b is removed.

Now, the switching switch 72 in this post-processing circuit 45 is switched by the discriminating signal of, for example, one discriminating circuit 79d. For example, normally one signal processing part 44c side is selected. On the other hand, when the electronic scope 2D is connected, its type signal will be discriminated by the discriminating circuit 79d and the switching switch 72 will be switched so that the electronic scope 2D side may be selected as shown in FIG. 13.

The respective discriminating circuits 79c and 79d may be of the same formation as in the first embodiment. (However, in this embodiment, whether the mosaic type electronic scope 2D is connected or the mosaic type TV camera 5D is connected is determined).

The connector means, that is, the connector and connector receptacle may be the same as in the first embodiment.

Figure 14:
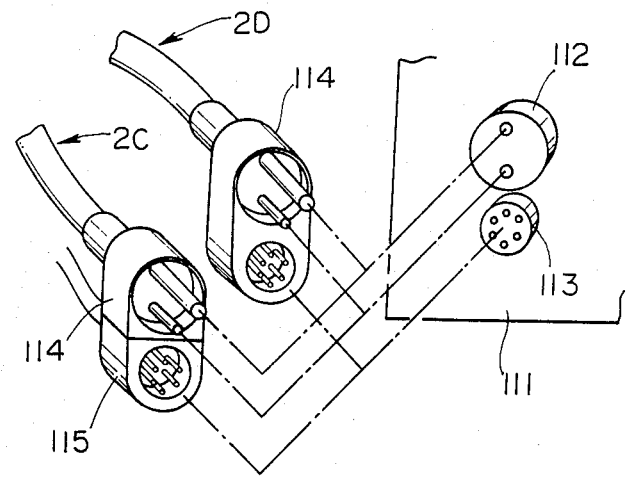
FIG. 14 is a perspective view showing a connector means in the second embodiment.

The above mentioned connector means are provided separately on the signal side but may be used in common as shown in FIG. 14. That is to say, the imaging apparatus body 111 is provided with the light source connector receptacle 112 and signal connector receptacle 113. On the other hand, the electronic scope 2D and the fiber scope 2C fitted with the TV camera are provided with the light source connector 114 and signal connector 115 fittable to the above mentioned respective connector receptacles 112 and 113. In the electronic scope 2D, these connectors 114 and 115 are made in one body.

The electronic scope 2D is provided with a type signal generating circuit 22D different from the TV camera 5C.

Figure 15:
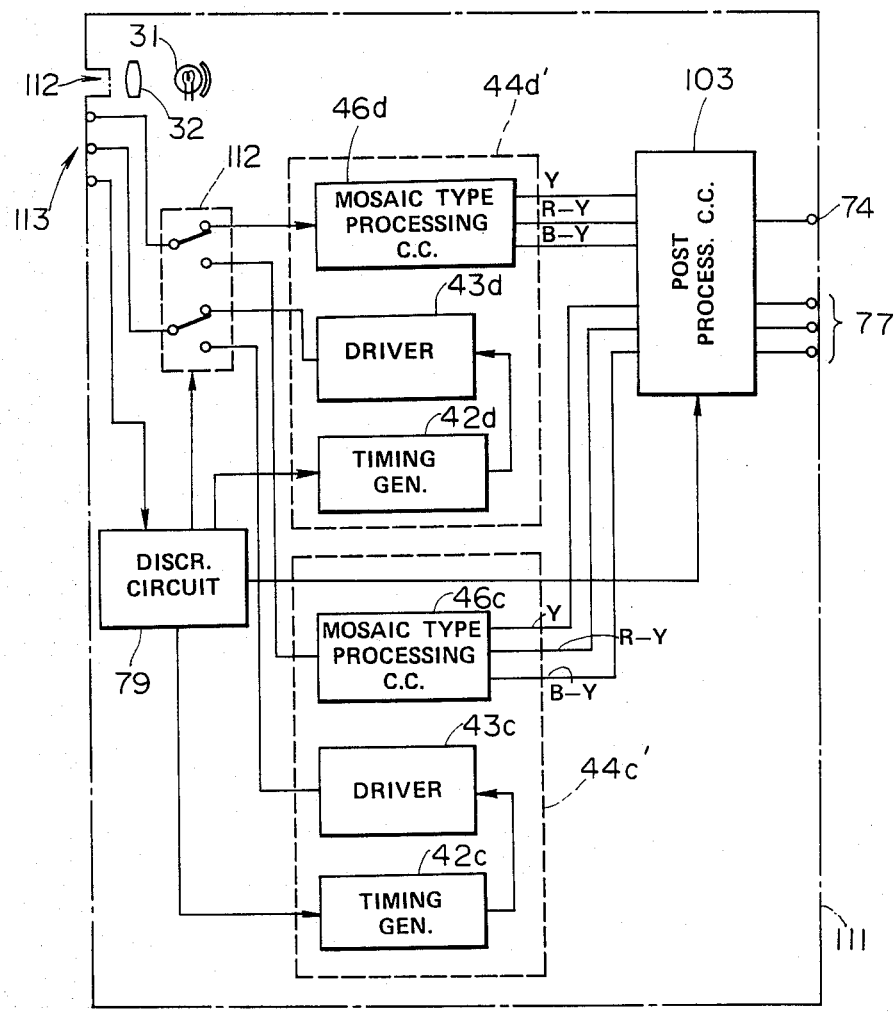
FIG. 15 is a formation view showing an imaging apparatus body in the third embodiment of the present invention.

On the other than, the imaging apparatus body 111 is formed as shown, for example, in FIG. 15.

This imaging apparatus body 111 is made a common discriminating circuit 79 in the imaging apparatus body 101 shown in FIG. 13. The switching switch 112 is switched in response to the scope 2C or 2D connected by the discriminating circuit 79 and the switching switch 72 of the post-processing circuit 103 can be also switched.

The signal processing parts 44c' and 44d' are the same except that the signal processing parts 44c and 44d shown in the above mentioned FIG. 13 and the discriminating circuit 79b and 79c are made common.

In this third embodiment, if the connector of the used scope 2C or 2D is merely connected, the signal corresponding to the connected scope will be processed and can be color-displayed by the color monitor. The fiber scope 2A can be used.

Figure 16:
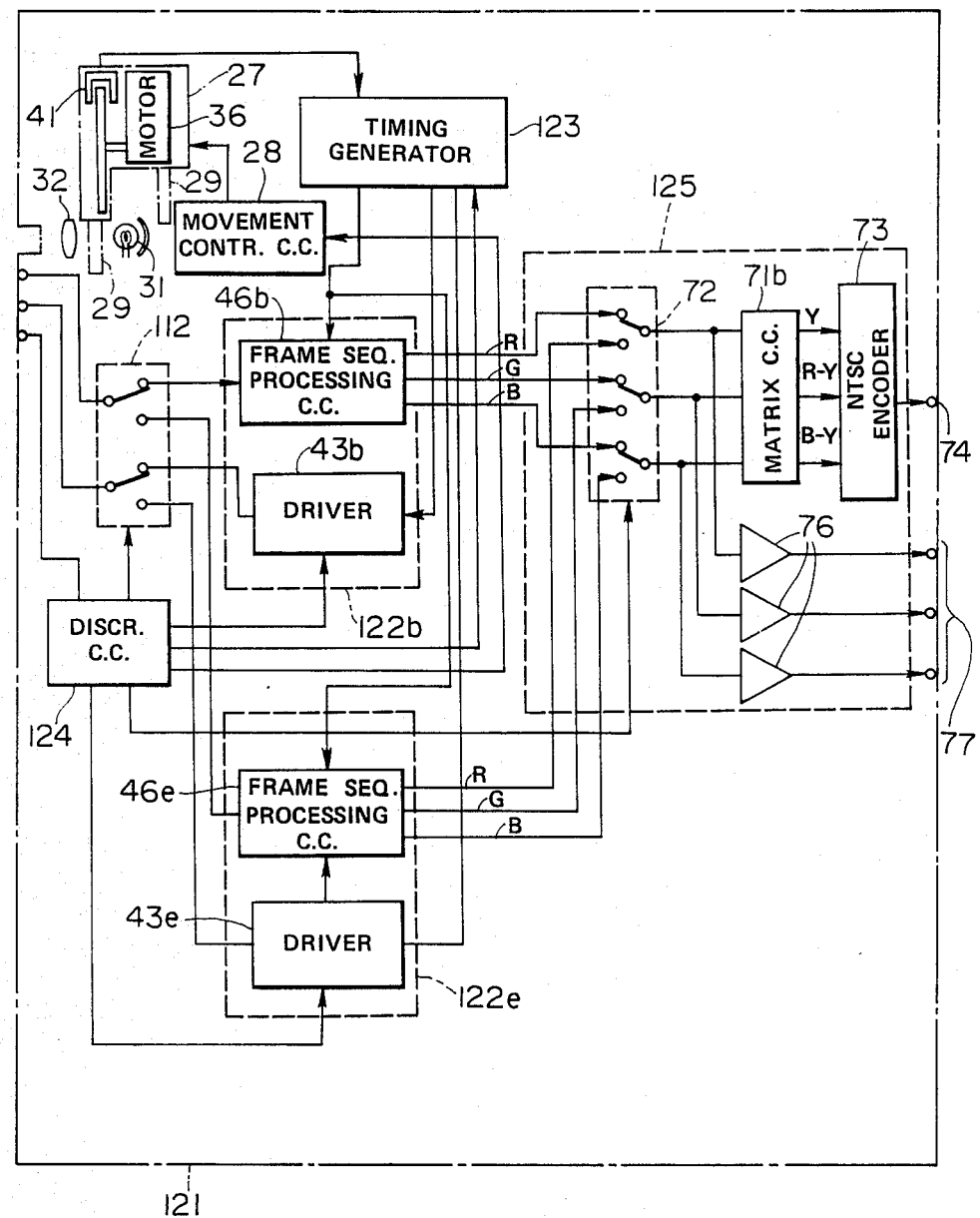
FIG. 16 is a formation view showing an imaging apparatus body in the fourth embodiment of the present invention.

FIG. 16 shows the fourth embodiment of the present invention wherein even the frame sequential type electronic scope 2B and the fiber scope 2A fitted with the frame sequential type TV camera 5E, that is, the fiber scope 2E fitted with the frame sequential type TV camera can be used.

In this imaging apparatus body 121, two frame sequential type signal processing parts 122b and 122c are provided and a timing generator 123 and discriminating circuit 124 are commonly used. The frame sequential type processing circuit 46b and the driver 43b forming one signal processing part 122b are for the frame sequential type electronic scope 2B the same as in the first embodiment. The other signal processing part 122e is for the fiber scope 2E fitted with the frame sequential type TV camera 5E shown in FIG. 17. These two processing circuits 46b and 46e and the drivers 43b and 43e are provided in response to different numbers of pixels. Their formations are the same.

In the post-processing circuit 125 in this embodiment, for example, the outputs of both processing circuits 46b and 46e are switched by the switching switch 72 and then R, G and B signals are output from the RGB output end 77 respectively through the buffers 76. The R, G and B signals through the above mentioned switching switch 72 are separated into a luminance signal Y and color difference signals R-Y and B-Y, are converted to a composite video signal of an NTSC type by an NTSC encoder 73 and a composite video signal is output from the NTSC output end 74.

Figure 17:
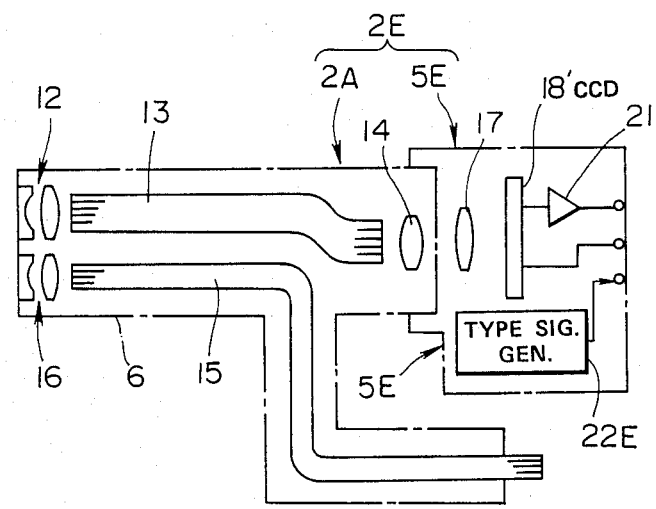
FIG. 17 is a schematic formation view of a fiber scope fitted with a frame sequential type TV camera.

The above mentioned frame sequential type TV camera 5E is of the formation shown in FIG. 17. This frame sequential type TV camera 5E is of the structure of the color mosaic type TV camera 5C of FIG. 5 wherein no color mosaic filter 19 is provided. In this case, too, a CCD 18' having a layer number of pixels larger than the number of pixels of the CCD 18, used in the electronic scope 2B, is used.

In this embodiment, when the frame sequential type electronic scope 2B or the fiber scope 2E fitted with the TV camera is connected, in either case, the type signal output from the type signal generating circuit 22B or 22E is discriminated and the movable filter part 27 is moved to make a frame sequential type illumination. Also, the above mentioned type signal is set to be different between both scopes 2B and 2E and is discriminated by the discriminating circuit 124. The switching switch 112 is switched so that the signal processing part 122b or 122e may be selected in response to the connected scopes 2B and 2E and the switching switch 71b of the signal converting output circuit 125 is also switched.

The above mentioned discriminating circuit 124 outputs a discriminating signal operating a signal processing system corresponding to the connected scope 2B or 2E for the timing generator 123. Further, this discriminating circuit 124 operates the driver 122b or 122e on the signal processing system side corresponding to the connected scope 2B or 2E. The above mentioned timing generator 123 outputs a timing signal at the time of the end of the R, G and B frame sequential illuminations to the driver 122b or 122e on the basis of the discriminating signal output from the discriminating circuit 124, applies driving pulses to the connected scope 2B or 2E from the driver 122b or 122e and reads the signal out of the CCD 18 or 18'.

This fourth embodiment is of an operation similar to the operation when the frame sequential type electronic scope 2B in the first embodiment is connected except that a switching operation accompanies the common use of the timing generator 123 and discriminating circuit 124.

When only the fiber scope 2A is connected, a white illumination will be made.

Now, in the above mentioned first embodiment, the electronic scope is of a frame sequential type and the TV camera is of a mosaic type. On the contrary, in case the electronic scope is of a mosaic type and, on the other hand, the TV camera is of a frame sequential type, the signal process corresponding to a different number of pixels may be made with the formation of two signal processing parts 44b and 44c in the first embodiment.

Figure 18:
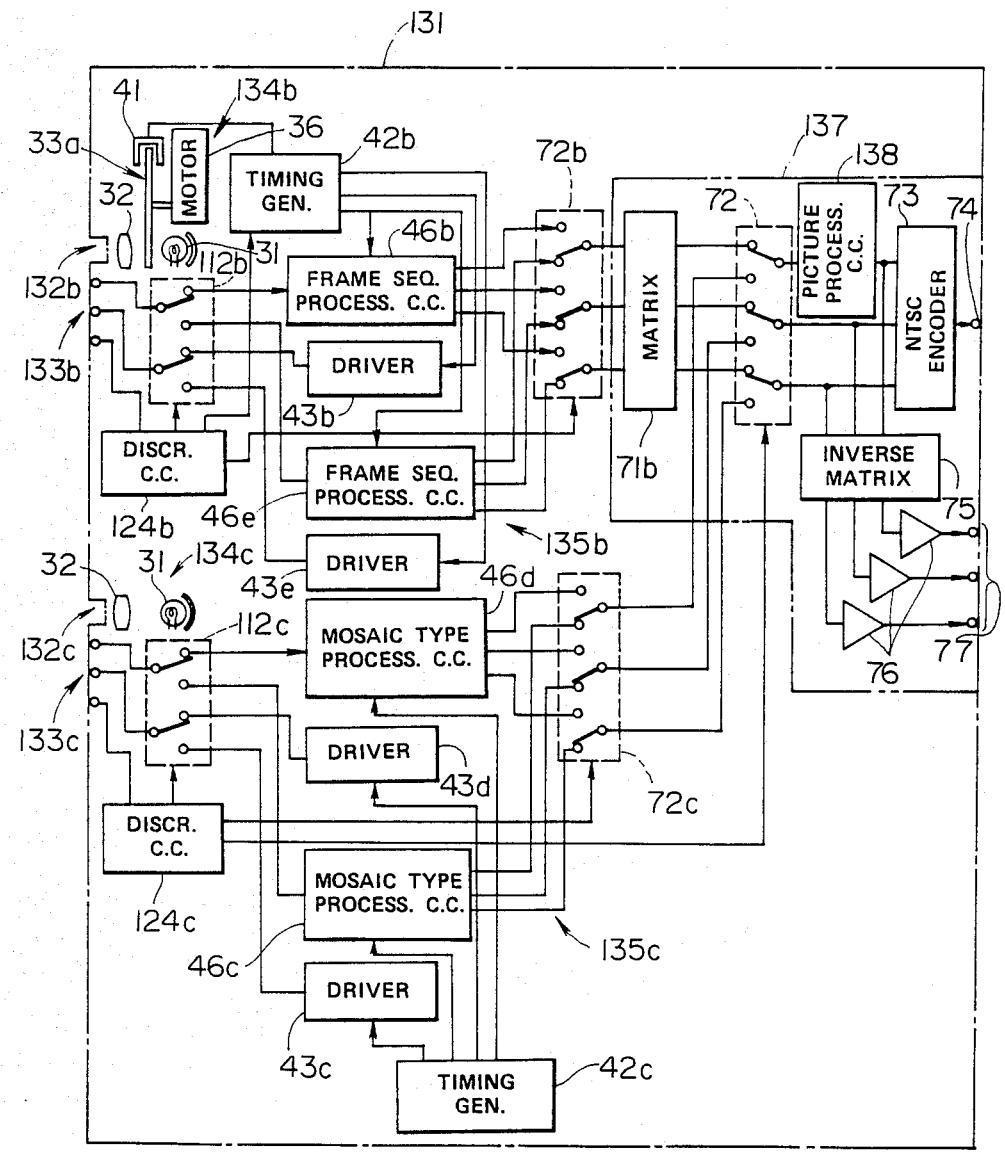
FIG. 18 is a formation view of an imaging apparatus body in the fifth embodiment of the present invention.

FIG. 18 shows the fifth embodiment of the present invention.

In this embodiment, any of the frame sequential type electronic scope 2B, mosaic type electronic scope 2D, fiber scope 2E fitted with the frame sequential type TV camera, fiber scope 2C fitted with the mosaic type TV camera and fiber scope 2A can be used.

The imaging apparatus body 131 is provided on its housing front surface or the like with frame sequential type light source and signal connector receptacles 132b and 133b and mosaic type light source and signal connector receptacles 132c and 133c and within it with a frame sequential type light source part 134b and signal processing part 135b and a mosaic type light source part 134c and signal processing part 135c.

The above mentioned frame sequential type signal processing part 135b is of the same formation as is shown in FIG. 16. The mosaic type signal processing part 135c is of substantially the same formation as the formation in which the frame sequential type process circuits 46b and 46e are replaced with the mosaic type processing circuits 46c and 46d in the frame sequential type signal processing part in FIG. 16.

The post-processing circuit 137 is of a formation in which a line interpolating picture image processing circuit 138 is replaced instead of the outline enhancing circuit 78.

The field sequential side discriminating circuit 124b discriminates on the basis of the type signal whether the connected scope is the frame sequential type electronic scope 2B or the fiber scope 2E fitted with the frame sequential type TV camera and switches the switching switches 112b and 72b.

In the same manner, the mosaic type side discriminating circuit 124c discriminates whether the connected scope is the mosaic type electronic scope 2D or the fiber scope 2C fitted with the mosaic type TV camera and switches the switching switches 112c and 72c. When this discriminating circuit 124c senses that either of the mosaic type scopes 2C and 2D is connected, the switching switch 72 of the signal converting output circuit 137 will be switched so that the output signal of the mosaic type signal processing part 135 may be conductive.

The fiber scope 2A can be used by connecting its connector to the mosaic type light source connector receptacle 132.

According to this embodiment, electronic scopes of both systems or fitted with TV cameras can also be used.

Now, in the system of each of the above described embodiments, not only the fiber scope 2A is used as an optical endoscope but also a rigid endoscope can be used. For example, in the system 1 of the first embodiment, the fiber scope 2A and the fiber scope 2C fitted with the TV camera 5C in the fiber scope 2A and the rigid endoscope 102F shown in FIG. 19 and the rigid endoscope 102G fitted with the mosaic type TV camera which is this rigid endoscope 102F fitted with the mosaic type TV camera 103 can be also used. (Needless to say, they can be used instead of the fiber scope 2A to form systems.)

Also, instead of the fiber scope 2E fitted with the frame sequential type TV camera shown in FIG. 17, as shown in FIG. 20, a rigid endoscope 102H fitted with a frame sequential TV camera which is the rigid endoscope 102F fitted with the frame sequential type TV camera 104 can be also used.

In the above mentioned rigid endoscope 102F, as shown in FIG. 21, a light guide 106 is inserted through a rigid insertable part 105 and is fixed in the end part on the base side with a light guide mouthpiece 108 of a gripping part 107. A light guide cable 109 can be connected to this light guide mouthpiece 108. On this light guide cable 109, a light guide connector 110 is formed. The illuminating light fed from the light source part is transmitted to the light guide and is emitted from the exit end surface on the tip side of the insertable part 105. The image of an object illuminated by the illuminating light emitted from this exit end surface is formed in the focal plane by an objective 111 fitted to the tip part. The optical image formed by this objective 111 is transmitted to the exit end side on the eyepiece part 114 side by a relay optical system 103 (as an image guide means) fitted within a rigid lens tube 112. The object can be observed with a naked eye through an eyepiece 115 arranged within the eyepiece part 114. Also, by fitting a removable TV camera 103 or 104 to this eyepiece part 114, the image can be formed on the imaging surface of the CCD 18' by the image forming lens 116. A color separating mosaic filter 118 is fitted to the imaging surface of the CCD 18' in the mosaic type TV camera 103.

A signal cable 119 is connected from the above mentioned TV cameras 103 and 104 and is fitted in the end parts respectively with signal connectors 120G and 120H.

The TV cameras 103 and 104 contain respectively type signal generating circuits (abbreviated as T.S.G.) 121G and 121H outputting type signals showing respectively that they are mosaic type and frame sequential type color imaging means.

In the above mentioned rigid endoscope 102F, a relay optical system 113 in which a plurality of convex lenses are arranged in a column is used as an image guide transmitting optical images and therefore an optical image of a resolution generally higher than of the fiber scope 2A formed of a fiber bundle as an image guide is obtained.

Therefore, when a TV camera 103 or 104 using the CCD 18' of a large number of pixels is fitted to the eyepiece part 114 of this rigid endoscope 2A, an imaged picture image of the resolution higher than of the electronic scope, in which an SID must be contained within a fine diameter insertable part, can be obtained. Therefore, using the CCD 18' of a large number of pixels for an externally fitted camera 103 or 104 is large.

Further, in case an electronic endoscope is formed by fitting a TV camera to the eyepiece part of this optical endoscope following the optical endoscope, the (optical) observed image accumulated until then can be effectively utilized as diagnosing data.

Another embodiment which can be formed by partly combining the respective embodiments, and belongs to the present invention.

What is claimed is:
1. An endoscope imaging system comprising:
   an electronic endoscope having,
      an elongate insertable part,
      an imaging means for imaging an object, said imaging means consisting of a first objective optical system fitted to said insertable part and a solid state imaging device arranged in a focal plane of said objective optical system, and
      a light emitting means, arranged on said insertable part, for illuminating said object;
   an optical endoscope having,
      an elongate insertable part,
      an observing optical system having a second objective optical system fitted to the insertable part of the optical endoscope,
      an optical image guide transmitting an optical image formed by said second objective optical system to an eyepiece part side on which an exit end surface side arranged,
      a light emitting means arranged on the insertable part of the optical endoscope, and
      a television camera fittable to said eyepiece part side of said optical endoscope and containing an imaging means consisting of a solid state imaging device with a number of pixels larger than that of said solid state imaging device of said electronic endoscope;

a signal processing means for processing signals corresponding to the respective imaging means of said electronic endoscope and said television camera; and a monitor means for displaying predetermined video signals output from said signal processing means.

2. An endoscope imaging system according to claim 1 wherein said light emitting means is formed of a light guide, said light guide has an exit end surface and an entrance end, said light guide emitting an illuminating light, input to the entrance end, from said exit end surface.

3. An endoscope imaging system according to claim 2 further has a light source means for feeding the illuminating light to said light guide.

4. An endoscope imaging system according to claim 3 wherein said light source generates a white light.

5. An endoscope imaging system according to claim 3 wherein said light source means sequentially outputs light of three wavelength ranges which are different from one another.

6. An endoscope imaging system according to claim 3 wherein said light source means outputs a white light and a frame sequential light of three wavelength ranges which are different from one another in a time series as switched by a switching means.

7. An endoscope imaging system according to any one of claims 1, 3, 4, 5 or 6 wherein said optical endoscope is formed of a fiber scope and wherein said optical image guide is formed of a fiber bundle.

8. An endoscope imaging system according to any one of claims 1, 5 or 6 wherein said optical endoscope is formed of a rigid endoscope wherein said optical image guide is formed of a relay optical system.

9. An endoscope imaging system according to any one of claims 1, 5 or 6 wherein said electronic endoscope is provided with a color-separating color filter in front of an imaging surface of said solid state imaging device.

10. An endoscope imaging system according to any one of claims 1, 3, 4, 5 or 6 wherein said electronic endoscope is a frame sequential color imaging type having no color separating color filter on an imaging surface of said solid state imaging device.

11. An endoscope imaging system according to any one of claims 1, 3, 4, 5 or 6 wherein said solid state imaging device contained in said television camera is fitted with a color-separating color filter in front of an imaging surface.

12. An endoscope imaging system according to any one of claims 1, 3, 4, 5 or 6 wherein said solid state imaging device contained in said television camera is of a frame sequential color imaging type having no color-separating color filter in front of an imaging surface.

13. An endoscope imaging system according to claim 9 wherein said signal processing means processes signals corresponding to said solid state imaging device provided with said color-separating color filter.

14. An endoscope imaging system according to claim 10 wherein said signal processing means processes signals corresponding to said frame sequential color imaging electronic endoscope.

15. An endoscope imaging system according to any one of claims 1 or 4 wherein said electronic endoscope and said television camera have an output signal different from one another.

16. An endoscope imaging system according to claim 15 wherein said signal processing means has a signal discriminating means.

17. An endoscope imaging system according to any one of claims 1 or 3 wherein said signal processing means has in common a signal processing system outputting a predetermined video signal.

18. An endoscope imaging system according to claim 17 wherein said signal processing system is controlled in switching by a discriminating means.

19. An endoscope imaging system according to claim 11 wherein said signal processing means is to process signals corresponding to said solid state imaging device provided with said color-separating color filter.

20. An endoscope imaging system according to claim 12 wherein said signal processing means is to process signals corresponding to said frame sequential color imaging type.

21. An endoscope imaging system comprising:
an electronic endoscope having,
an elongate insertable part,
an imaging means for imaging an object, said imaging means consisting of a first objective optical system fitted to said insertable part and a solid state imaging device arranged in a focal plane of said objective optical system, and
a light emitting means, arranged on said insertable part, for illuminating said object;
an optical endoscope having,
an elongate insertable part,
an observing optical system having a second objective optical system fitted to the insertable part of the optical endoscope,
an optical image guide transmitting an optical image formed by said second objective optical system to an eyepiece part side on which an exit end surface side is arranged,
a light emitting means arranged on the insertable part of the optical endoscope, and
a television camera fittable to said eyepiece part side of said optical endoscope and containing an imaging device consisting of a solid state imaging device with a number of pixels larger than that of said solid state imaging device of said electronic endoscope; and
a signal processing means for processing signals corresponding to the respective imaging means of said electronic endoscope and said television camera.

22. An endoscope imaging system comprising:
an electronic endoscope having,
an elongate insertable part,
an imaging means for imaging an object, said imaging means consisting of a first objective optical system fitted to said insertable part and a solid state imaging device arranged in a focal plane of said objective optical system, and
a light emitting means, arranged on said insertable part, for illuminating said object;
an optical endoscope having,
an elongate insertable part,
an observing optical system having a second objective optical system fitted to the insertable part of the optical endoscope,
an optical image guide transmitting an optical image formed by said second objective optical system to an eyepiece part side on which an exit end surface side is arranged, a light emitting means arranged on the insertable part of the optical endoscope, and a television camera fittable to said eyepiece part side of said optical endoscope and containing an imaging means consisting of a solid state imaging device with a number of pixels larger than that of said solid state imaging device of said electronic endoscope; and a light source providing illuminating light to an incident plane of said light emitting means of said electronic endoscope or optical endoscope.

23. The endoscope imaging apparatus according to claim 21 or 22 wherein said optical endoscope fitted with said television camera is a fiber scope transmitting an optical image by an image guide fiber bundle.

24. The endoscope imaging apparatus according to claim 21 or 22 wherein said optical endoscope fitted with said television camera is a rigid endoscope transmitting an optical image by a relay optical system.

25. The endoscope imaging apparatus according to claims 21 or 22 wherein said television camera has a mounting means fittable to said eyepiece part of said optical endoscope.

* * * * *